United States Patent [19]

Atwell

[11] Patent Number: 4,870,978
[45] Date of Patent: Oct. 3, 1989

[54] METHOD OF FORMING AN ADJUSTABLE TOURNIQUET DEVICE

[76] Inventor: Sharon L. Atwell, 10211 Schaper Dr., Galveston, Tex. 77554

[21] Appl. No.: 185,798

[22] Filed: Apr. 25, 1988

[51] Int. Cl.$^4$ .............................................. A61B 17/12
[52] U.S. Cl. .................................... 128/898; 128/327; 289/1.5; 28/143
[58] Field of Search ................. 128/327, 898; 289/1.5, 289/1.2; 2/338; 28/143; 119/106

[56] References Cited

U.S. PATENT DOCUMENTS

| | | | |
|---|---|---|---|
| 1,424,458 | 8/1922 | Fleisher | 289/1.5 X |
| 1,743,452 | 1/1930 | Hatch | 128/327 |
| 3,156,243 | 11/1964 | Sculley | 128/327 |

FOREIGN PATENT DOCUMENTS

| | | | |
|---|---|---|---|
| 264763 | 10/1932 | Italy | 289/1.5 |
| 202436 | 8/1923 | United Kingdom | 119/106 |

Primary Examiner—Michael H. Thaler
Attorney, Agent, or Firm—Leon Gilden

[57] ABSTRACT

An adjustable tourniquet device is set forth wherein a predetermined length of surgical elastomeric tubing is doubled upon itself and subsequently knotted along the length to form a series of loops terminating in a final knot. The loops may be equally spaced or of decreasing opening size by varying the spacing between the sequential knots. The device is positionable about a victim's limb whereupon the device is extended about the limb and the final knot is positioned through one of the loops to provide adequate pressure on the limb to limit circulation consistent with tourniquet use. The decreasing loops of the tourniquet provide an extra measure of adjustment in use by enabling incrementally smaller diametrical application of the tourniquet.

1 Claim, 1 Drawing Sheet

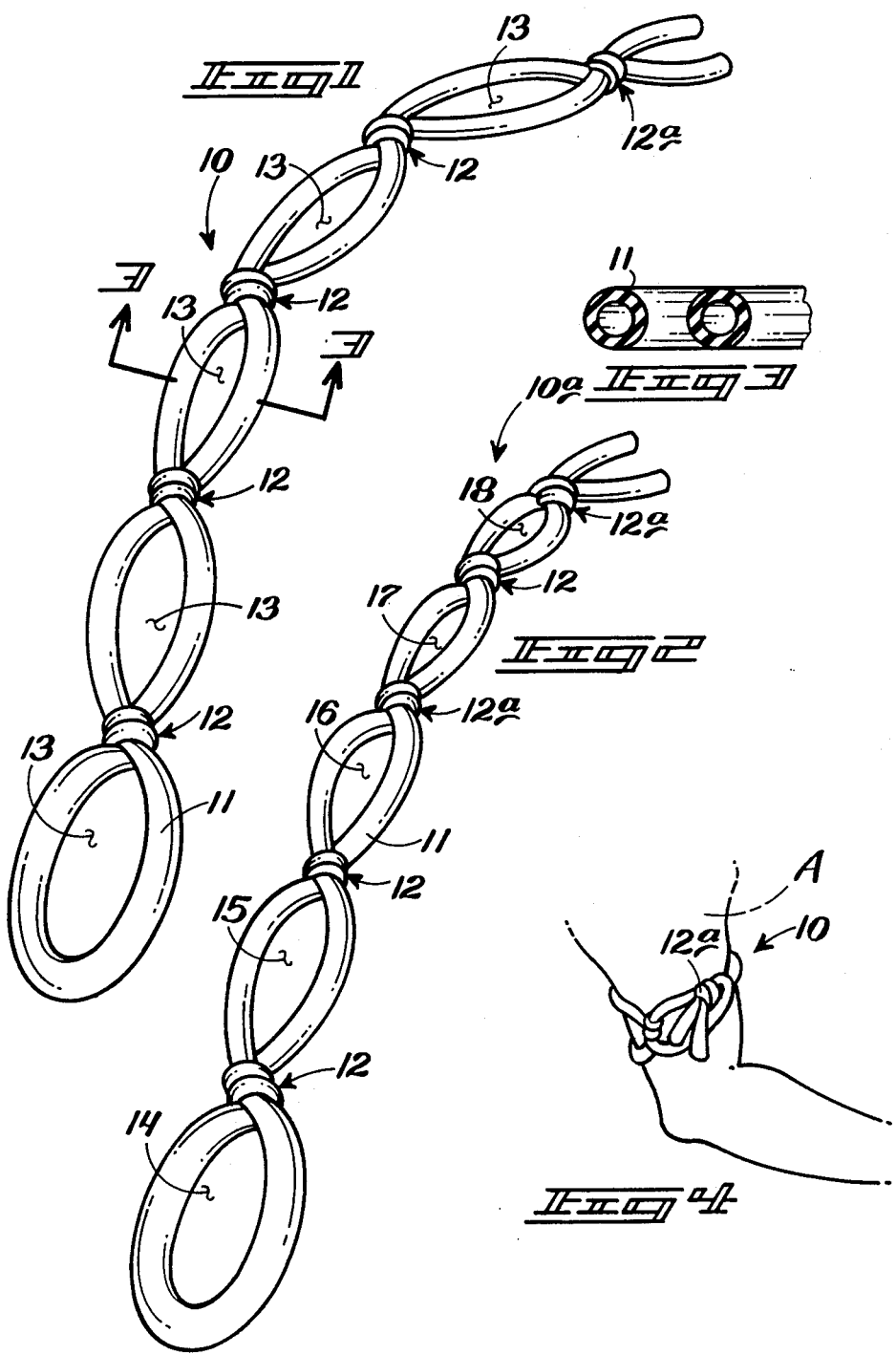

METHOD OF FORMING AN ADJUSTABLE TOURNIQUET DEVICE

BACKGROUND OF THE INVENTION

1. Field of the Invention

The field of invention relates to tourniquets and more specifically to a new and improved tourniquet formed of hollow surgical tubing provided with a great degree of inherent resiliency and strength in use.

2. Description of the Prior Art

The use of tourniquets and their application to limbs for limiting circulation of blood to a lower extremity of a limb preventing unnecessary blood loss is well known in the prior art. Tourniquets in the past have generally been of simplistic construction and have utilized strap-like materials frequently requiring manual maintenance to maintain pressure on an associated limb. Prior art devices have been developed for selfsecuring tourniquets, but have generally been of unnecessarily complex construction or organization to limit their use and manufacture. Examples of prior art devices include U.S. Pat. No. 1,607,996 to Morganthaler wherein a beaded chain has secured at one terminal end thereof a connecting member to enable latching of the chain to the connecting member when secured about a limb. the patent is of interest relative to the use of a self-locking tourniquet, but is of a structure relatively remote from that of instant invention.

U.S. Pat. No. 2,519,712 to Stegman sets forth a tourniquet formed as a belt formed with a series of parallel openings therethrough for cooperation with projections formed in said belt in an offset array to said projection to enable securement of the flexible belt about an associated limb and further including the use of a hand-grafting portion for maintaining interlocking relationship between the projections and openings. The patent includes a plural layer construction and accordingly is of a relatively complex and distant organization to that of the instant invention.

U.S. Pat. No. 3,156,243 to Sculley sets forth the use of a resilient single tubular member formed with a single loop at one end terminating in a bulbous member secured at that end with an enlarged other tubular end for positioning through the single loop and maintained in a locked position by the additional bulbous end. The Sculley patent is accordingly of limited application as compared to the instant invention by utilizing a single loop for cooperation with an enlarged elongate tubular end and lacks the adjustability and simplicity of construction of the instant invention.

U.S. Pat. No. 3,390,680 to Marcum sets forth a tourniquet device including a plurality of sleeves spaced along a strip in a developing relationship with respect to a tab with a second series of sleeves spaced along the strip wherein stretching of the strip permits movement of said strip within said first sleeves between adjacent formed anchoring lines on said strip wherein Velcro surfaces formed between said various elements permits securing of said tourniquet about a desired limb.

U.S. Pat. No. 3,756,239 to Smithe sets forth an inflatable tourniquet formed as an elongate flexible tube for encircling a limb with an inlet opening and is secured by having a fitting projecting through selected openings in the associated strap so that upon inflation of the tub, the strap will remain securely wrapped in a predetermined orientation with respect to the limb.

As may be appreciated, however, there is a continuing need for a new and improved adjustable tourniquet of simplified construction and application for effective and efficient application of pressure to an associated limb and in this respect, the present invention substantially fulfills this need.

SUMMARY OF THE INVENTION

In view of the foregoing disadvantages inherent in the known types of tourniquets now present in the prior art, the present invention provides an adjustable tourniquet wherein a series of constant or alternatively decreasing loop sizes along a length of flexible surgical tubing enables a myriad of adjustment positions of said tourniquet about an associated limb. As such, the general purpose of the present invention, which will be described subsequently in greater detail, is to provide a new and improved adjustable tourniquet which has all the advantages of the prior art tourniquets and none of the disadvantages.

To attain this, the present invention comprises a tourniquet which may be compactly stored during periods of nonuse and further including a finite length of flexible tubing overfolded upon itself and knotted throughout the overfolded length of the strip to present a series of loops bounded by the aforenoted knots whereupon a final knot is registrable with any of the series of loops to provide desired constriction to an associated limb during use.

My invention resides not in any one of these features per se, but rather in the particular combination of all of them herein disclosed and claimed and it is distinguished from the prior art in this particular combination of all of its structures for the functions specified.

There has thus been outline, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the pbulic generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved adjustable tourniquet which has all the advantages of the prior art adjustable tourniquets and none of the disadvantages.

It is another object of the present invention to provide a new and improved adjustable tourniquet which may be easily and efficiently manufactured and marketed.

It is a further object of the present invention to provide a new and improved adjustable tourniquet which is susceptible of a low cost of manufacture with regard to both materials and labor, and which accordingly is then susceptible of low prices of sale to the comsuming public, thereby making such adjustable tourniquets economically available to the buying public.

Still yet another object of the present invention is to provide a new and improved adjustable tourniquet which provides in the apparatuses and methods of the prior art some of the advantages thereof, while simultaneously overcoming some of the disadvantages normally associated therewith.

Still another object of the present invention is to provide a new and improved adjustable tourniquet formed of flexible and resilient surgical tubing overfolded upon itself and formed into a series of loops and knots terminating in a final knot that is registrable with any of the series of so-formed loops for securement of the tourniquet about an associated limb in an adjustable manner.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an isometric illustration of the instant invention illustrating a series of the loops and knots in the formation of the tourniquet.

FIG. 2 is an isometric illustration of a further embodiment of the instant invention illustrating a series of loops of decreasing ties to provide a finer adjustment of the tourniquet about as associated limb.

FIG. 3 is an isometric illustration taken along the lines 3—3 of FIG. 1 in the direction indicated by the arrows.

FIG. 4 is an isometric illustration of the instant invention secured about an associated limb.

DESCRIPTION OF THE PREFERRED EMBODIMENT

With reference now to the drawings, and in particular to FIGS. 1 to 4 thereof, a new and improved adjustable tourniquet device embodying the principles and concepts of the present invention and generally designated by the reference numerals 10 and 10a will be described.

More specifically, with reference to FIG. 1 it will be noted that the adjustable tourniquet device is essentially formed of a finite length of resilient flexible surgical-type tubing 11. The tubing is generally of synthetic rubber-like material including a relatively high co-efficient of friction for creating a non-slip intercommunicating relationship with itself in the formation of knots 12 and upon application of the device, as illustrated in FIG. 4, to maintain a non-slip relationship with itself in use.

Essentially the tubing 11 is overfolded upon itself to create substantially a second length of tubing of essentially half the original length whereupon the tubing is knotted upon itself or may utilize auxiliary fasteners to create a series of knots along the second finite length of tubing, as illustrated in FIG. 1. The knots 12 accordingly create a series of loops 13 of possibly equal length and of opening size to provide a large degree of adjustability upon application of the tourniquet about an arm to similar limb. The inherent resiliency of surgical-type tubing of this character and classification enables the tourniquet, as illustrated in FIG. 4 in use, to stretch and accordingly enable a terminal knot 12a formed at a forwardmost end of the tourniquet device 10 to project through any one of the loops 13 to provide a desired pressure about an associated arm "A", for example, to constrict flow of blood and effect a tourniquet to arm "A".

Reference to FIG. 2 illustrates a modification of the instant invention wherein the knots 12 terminating in a terminal knot 12a, as in the device illustrated in FIG. 1, creates a series of loops including a first loop 14, a second loop 15, a third loop 16, a fourth loop 17, and a fifth loop 18, of respective decreasing lengths and openings to effect a greater degree of adjustability of the tourniquet in use. The decreasing loop sizes enables the use of a greater number of loops for a given length of overfolded tubing and the greater number of openings to accordingly enable a finer adjustment of the tourniquet about a limb by providing a user with a greater number of loops to choose from the provide a desired pressure in application to the tourniquet.

The number of loops so created should be at least three and not to exceed ten in construction of the tourniquet of the instant invention as this has been discovered to be the range of practical application of the device to accommodate limbs of varying diameters.

As to the manner of usage and operation therefore of the present invention should be apparent from the above description. Accordingly no further discussion relative to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A method of forming a tourniquet device comprising providing a first finite length of elastomeric resilient tubing, and subsequently doubling said tubing upon itself by overfolding said length of elastomeric tubing upon itself to form a second finite length of said tubing, and knotting said tubing along the formed second finite length to create a series of loops and a series of knots terminating in a terminal knot, and projecting said terminal knot through one of said series of loops to effect a constricting force upon a limb requiring a tourniquet application, and wherein said loops are formed of decreasing size as measured from a first loop formed by a first knot terminating in a final loop proximate said terminal knot, and wherein said knotting includes knotting said tubing upon itself, and wherein said step of providing a finite length of elastomeric tubing includes providing tubing including a high co-efficient of friction for effecting a non-slip intercommunication with said tubing to itself in formation of knots and in application of said device as a tourniquet, and wherein the step of creating a series of loops includes forming at least three to ten loops.

* * * * *